(12) United States Patent
Jugl et al.

(10) Patent No.: US 11,484,662 B2
(45) Date of Patent: Nov. 1, 2022

(54) MEDICAMENT INJECTION DEVICE

(71) Applicant: Sanofi-Aventis Deutschland GMBH, Frankfurt am Main (DE)

(72) Inventors: Michael Jugl, Frankfurt am Main (DE); Axel Teucher, Frankfurt am Main (DE); Stefan Blancke, Frankfurt am Main (DE); Michael Helmer, Frankfurt am Main (DE); Marc Schader, Frankfurt am Main (DE); Sebastian Braun, Darmstadt (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 167 days.

(21) Appl. No.: 15/778,263

(22) PCT Filed: Nov. 21, 2016

(86) PCT No.: PCT/EP2016/078262
§ 371 (c)(1),
(2) Date: May 23, 2018

(87) PCT Pub. No.: WO2017/089273
PCT Pub. Date: Jun. 1, 2017

(65) Prior Publication Data
US 2018/0339111 A1    Nov. 29, 2018

(30) Foreign Application Priority Data
Nov. 27, 2015   (EP) ..................................... 15196693

(51) Int. Cl.
*A61M 5/32*   (2006.01)
*A61M 5/24*   (2006.01)
(Continued)

(52) U.S. Cl.
CPC ............. *A61M 5/3202* (2013.01); *A61M 5/24* (2013.01); *A61M 5/178* (2013.01); *A61M 5/20* (2013.01);
(Continued)

(58) Field of Classification Search
CPC ...... A61M 5/3202; A61M 5/321; A61M 5/24; A61M 5/2033; A61M 5/20; A61M 5/348;
(Continued)

(56) References Cited

U.S. PATENT DOCUMENTS 3,401,693 A    9/1968   Cohen
3,757,779 A *  9/1973   Rovinski ............... A61M 5/284
                                                    604/190
(Continued)

FOREIGN PATENT DOCUMENTS

EP    0584569       3/1994
JP    H05-068508 U  9/1993
(Continued)

OTHER PUBLICATIONS

International Search Report and Written Opinion in International Application No. PCT/EP2016/078262, dated Feb. 9, 2017, 10 pages.
(Continued)

*Primary Examiner* — Emily L Schmidt
*Assistant Examiner* — Antarius S Daniel
(74) *Attorney, Agent, or Firm* — Fish & Richardson P.C.

(57) ABSTRACT

A medicament delivery device comprising: a main body arranged to receive a medicament cartridge sealed with a penetrable barrier; a needle carrier carrying a needle; a cap removably coupled to the needle carrier, a pre-stressed spring connected to the needle carrier and to the main body, wherein the pre-stressed spring is held by an activation element coupled to the cap, wherein the activation element
(Continued)

is arranged to release the spring when the cap is pulled in a distal direction from the device, thereby causing the needle carrier to move axially in a proximal direction.

16 Claims, 4 Drawing Sheets

(51) Int. Cl.
    *A61M 5/34* (2006.01)
    *A61M 5/178* (2006.01)
    *A61M 5/20* (2006.01)

(52) U.S. Cl.
    CPC ..... *A61M 5/348* (2013.01); *A61M 2005/2474* (2013.01)

(58) Field of Classification Search
    CPC .... A61M 5/34; A61M 5/2455; A61M 5/3213; A61M 5/3216; A61M 2005/206; A61M 2005/2474; A61M 2005/1585
    See application file for complete search history.

(56) References Cited

U.S. PATENT DOCUMENTS

| | | | | |
|---|---|---|---|---|
| 3,825,003 A * | 7/1974 | Kruck | ............ | A61M 5/288 604/192 |
| 4,009,716 A * | 3/1977 | Cohen | ............ | A61M 5/288 604/192 |
| 4,966,591 A | 10/1990 | Yum | | |
| 5,380,287 A * | 1/1995 | Kikuchi | ............ | A61M 5/1454 604/135 |
| 5,858,008 A * | 1/1999 | Capaccio | ............ | A61J 1/2096 604/263 |
| 6,210,369 B1 * | 4/2001 | Wilmot | ............ | A61M 5/2033 604/157 |
| 2008/0249477 A1 * | 10/2008 | Paproski | ............ | A61M 5/326 604/198 |
| 2008/0269690 A1 | 10/2008 | Felix-Faure | | |
| 2012/0179109 A1 | 7/2012 | Takemoto et al. | | |
| 2013/0211345 A1 * | 8/2013 | Jugl | ............ | A61M 5/2466 604/240 |
| 2015/0119815 A1 | 4/2015 | Fuke et al. | | |
| 2015/0196718 A1 | 7/2015 | Radmer et al. | | |

FOREIGN PATENT DOCUMENTS

| | | |
|---|---|---|
| JP | 2008-307369 | 12/2008 |
| JP | 2014-503298 | 2/2014 |
| WO | WO 99/30759 | 6/1999 |
| WO | WO 2012/089821 | 7/2012 |
| WO | WO 2014/013594 | 1/2014 |

OTHER PUBLICATIONS

International Preliminary Report on Patentability in International Application No. PCT/EP2016/078262, dated May 29, 2018, 7 pages.

* cited by examiner

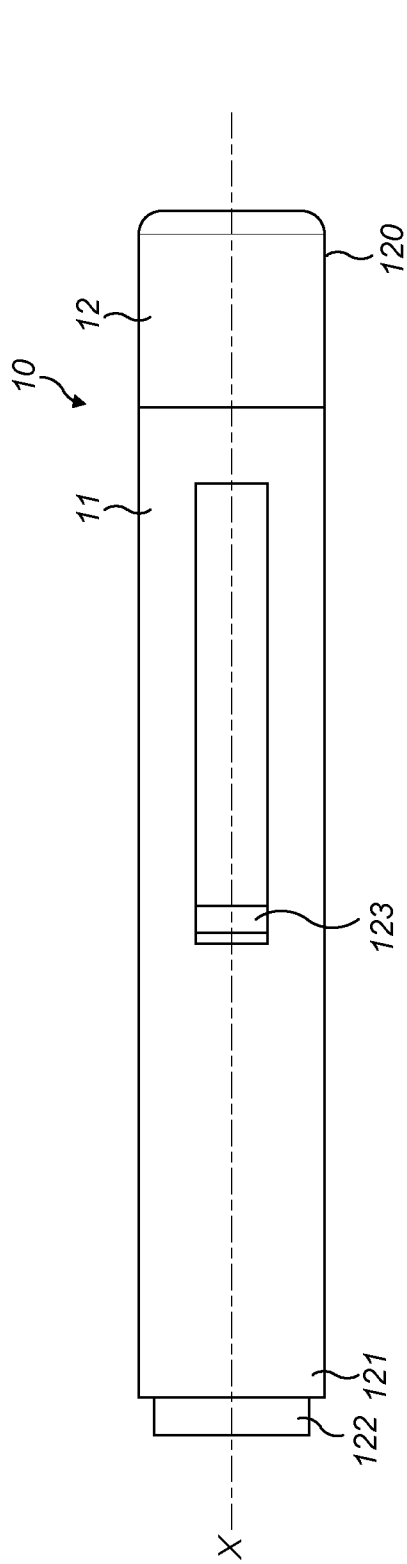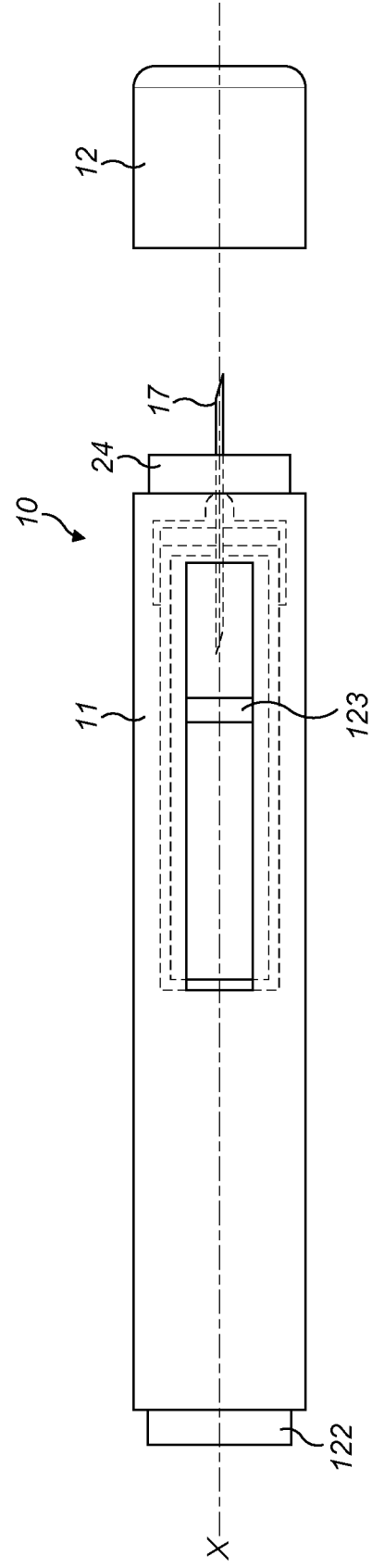

FIG. 4B
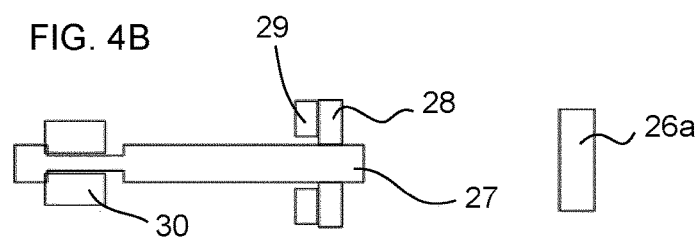
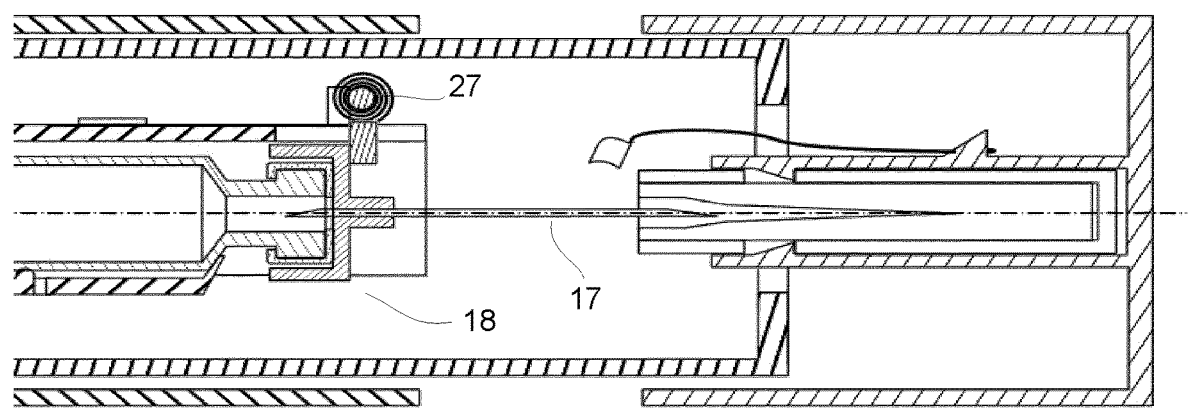
FIG. 4A

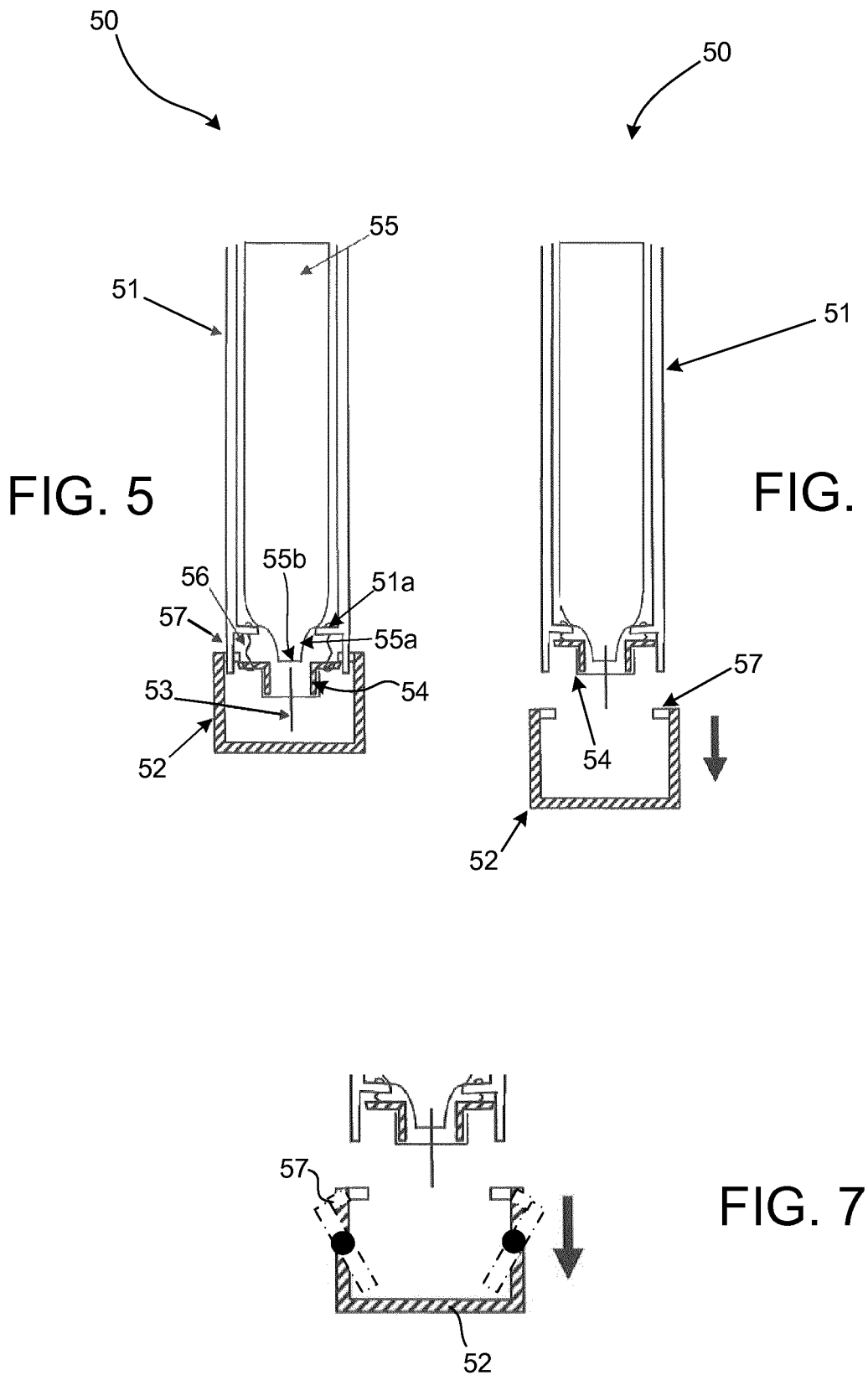

MEDICAMENT INJECTION DEVICE

CROSS REFERENCE TO RELATED APPLICATIONS

The present application is the national stage entry of International Patent Application No. PCT/EP2016/078262, filed on Nov. 21, 2016, and claims priority to Application No. EP 15196693.4, filed in on Nov. 27, 2015, the disclosures of which are incorporated herein by reference.

TECHNICAL FIELD

The present disclosure relates to medicament injection devices

BACKGROUND

Medicament injection devices can take the form of a syringe, whereby medicament is provided in a tubular barrel having a plunger and an outlet to which a needle is connected. A user connects the needle to the reservoir manually before the injection takes place. The attachment of the needle to the syringe requires some dexterity and is difficult for those having poor coordination, such as patients who have lost a degree of sensation in their hands.

While it is possible to provide injection devices in which the needle is pre-attached to a medicament cartridge, in certain situations it is desirable to provide a device in which the needle is kept separate from the medicament until such time as the user wishes to commence the injection.

SUMMARY

According to a first embodiment, there is provided a medicament delivery device comprising: a main body arranged to receive a medicament cartridge sealed with a penetrable barrier; a needle carrier carrying a needle; a cap removably coupled to the needle carrier, a pre-stressed spring connected to the needle carrier and to the main body, wherein the pre-stressed spring is held by an activation element coupled to the cap, wherein the activation element is arranged to release the spring when the cap is pulled in a distal direction from the device, thereby causing the needle carrier to move axially in a proximal direction.

The needle carrier may comprise a cup-shaped part configured to form a frictional fit with the medicament cartridge.

The cup-shaped part may have a lip to grip the medicament cartridge or the cartridge holder.

The device may further comprise a needle shield for shielding the distal end of the needle, wherein the needle shield is arranged to be fixed to the cap and removable from the needle.

The main body may comprise a cartridge holder for receiving the medicament cartridge.

The pre-stressed spring may be a constant force spring fixed, at a first end thereof, to the cartridge holder and, at a second end thereof, to a carrier attached to the needle carrier, wherein the constant force spring is held in a pre-stressed state by a removable portion of the activation element.

The pre-stressed spring may be a pull spring attached at a first end thereof to the main body and, at a second end thereof, to the needle carrier.

The pre-stressed spring may be a pull spring attached, at a first end thereof to the cartridge holder and, at a second end thereof, to the needle carrier.

The activation element may be a detent disposed on the interior of the cap.

The cap may have pivotable side walls that are arranged to release the detent when the cap is squeezed.

The detent may be releasable after rotationally aligning the cap with the needle holder.

The device may contain a medicament cartridge and axial movement of the needle carrier causes the needle to penetrate the penetrable barrier of the medicament cartridge.

The medicament cartridge may contain a medicament.

The device may be an auto-injector.

According to a second embodiment, there is provided a method of operating a medicament injection device having a cap, the method comprising: pulling the cap in a distal axial direction to remove the cap from the device to release a pre-stressed spring thereby causing proximal movement of a needle carrier needle, wherein a proximal end of the need is caused to pierce a penetrable barrier of a medicament cartridge.

BRIEF DESCRIPTION OF THE FIGURES

So that the disclosure can be fully understood, embodiments thereof will be described with reference to the accompanying drawings, in which:

FIGS. 1A and 1B are side-on views of an auto-injector device according to embodiments of the disclosure;

FIG. 4A is a side-on cross sectional schematic view of the distal end of the device shown in FIGS. 2 and 3 during a later stage of cap removal;

FIG. 4B is a schematic diagram of components of the device shown in FIG. 4A;

FIG. 5 is a side-on cross sectional schematic view of a device according to a second embodiment prior to cap removal;

FIG. 6 is a side-on cross sectional schematic view of the device shown in FIG. 5 subsequent to cap removal; and FIG. 7 shows a cap having pivotable sides.

DETAILED DESCRIPTION

Figure 2A:
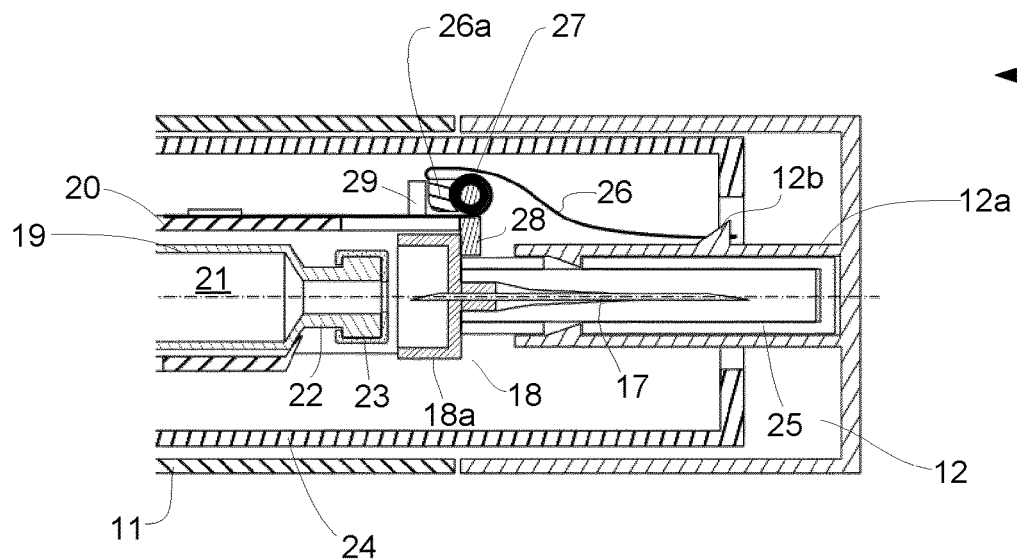
FIG. 2A is a side-on cross sectional schematic view of a distal end of a device according to a first embodiment.

Embodiments of the disclosure provide a mechanism for inserting the needle of an injection device such as an auto-injector or syringe into a medicament cartridge containing the medicament to be injected. Providing such a mechanism allows the medicament cartridge to be sealed until such time as the user wishes to commence the injection. Providing an automated mechanism for inserting the needle into the medicament cartridge also reduces the amount of handling of the needle by the user prior to the injection. Indeed, in embodiments of the disclosure the user does not need to touch the needle during the steps of inserting the needle into the medicament cartridge and subsequently actuating the injection of the medicament.

Embodiments of the disclosure make the needle insertion mechanism dependent on the removal of the device cap. A pre-stressed spring is coupled to the device body and to the needle holder which holds a needle. After assembly of the device and during storage, the fixation of the spring keeps the needle separate from the medicament cartridge. As the cap is removed, the spring is released causing the needle to pierce the septum of the medicament cartridge.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament into a patient's body. Device 10 includes a main body 11 which typically contains a reservoir containing the medicament to be injected (e.g., a syringe) and the components required to facilitate one or more steps of the delivery process. Device 10 can also include a cap assembly 12 that can be detachably mounted to the main body 11. Typically a user must remove cap 12 from main body 11 before device 10 can be operated.

As shown, main body 11 is substantially cylindrical and has a substantially constant diameter along the longitudinal axis X. The main body 11 has a distal region 120 and a proximal region 121. The term "distal" refers to a location that is relatively closer to a site of injection, and the term "proximal" refers to a location that is relatively further away from the injection site. Device 10 can also include a needle sleeve 24 coupled to main body 11 to permit movement of sleeve 24 relative to main body 11. For example, sleeve 24 can move in a longitudinal direction parallel to longitudinal axis X. Specifically, movement of sleeve 24 in a proximal direction can permit a needle 17 to extend from distal region 120 of main body 11.

Insertion of needle 17 can occur via several mechanisms. For example, needle 17 may be fixedly located relative to main body 11 and initially be located within an extended needle sleeve 24. Proximal movement of sleeve 24 by placing a distal end of sleeve 24 against a patient's body and moving main body 11 in a distal direction will uncover the distal end of needle 17. Such relative movement allows the distal end of needle 17 to extend into the patient's body. Such insertion is termed "manual" insertion as needle 17 is manually inserted via the patient's manual movement of main body 11 relative to sleeve 24.

Another form of insertion is "automated," whereby needle 17 moves relative to main body 11. Such insertion can be triggered by movement of sleeve 24 or by another form of activation, such as, for example, a button 122. As shown in FIGS. 1A & 1B, button 122 is located at a proximal end of main body 11. However, in other embodiments, button 122 could be located on a side of main body 11.

Other manual or automated features can include drug injection or needle retraction, or both. Injection is the process by which a bung or piston 123 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 121 of main body 11, and a distal end of the drive spring can be configured to apply a compressive force to a proximal surface of piston 123. Following activation, at least part of the energy stored in the drive spring can be applied to the proximal surface of piston 123. This compressive force can act on piston 123 to move it in a distal direction. Such distal movement acts to compress the liquid medicament within the syringe, forcing it out of needle 17.

Following injection, needle 17 can be retracted within sleeve 24 or main body 11. Retraction can occur when sleeve 24 moves distally as a user removes device 10 from a patient's body. This can occur as needle 17 remains fixedly located relative to main body 11. Once a distal end of sleeve 24 has moved past a distal end of needle 17, and needle 17 is covered, sleeve 24 can be locked. Such locking can include locking any proximal movement of sleeve 13 relative to main body 11.

Another form of needle retraction can occur if needle 17 is moved relative to main body 11. Such movement can occur if the syringe within main body 11 is moved in a proximal direction relative to main body 11. This proximal movement can be achieved by using a retraction spring (not shown), located in distal region 120. A compressed retraction spring, when activated, can supply sufficient force to the syringe to move it in a proximal direction. Following sufficient retraction, any relative movement between needle 17 and main body 11 can be locked with a locking mechanism. In addition, button 122 or other components of device 10 can be locked as required.

FIG. 2A shows a cross-sectional view of a distal end of a device 10. The device 10 has tubular main body 11 and a cap 12.

The cap 12 fits over a needle sleeve 24 and abuts the distal end of the main body 11. The cap 12 has an end wall and a curved side wall. The cap 12 comprises a tubular member 12a extending from the end wall of the cap 12. The tubular member is of a suitable diameter to receive a generally cylindrical needle shield 25 in which the distal end of a needle is stored. A frictional fit is formed between the tubular member 12a and the needle shield 25 containing the distal end of the needle 17 during assembly of the device 10. The frictional fit is sufficiently strong so that, as the cap 12 is removed, the needle shield 25 is also removed. The fit between the tubular member 12a and the needle shield 25 may also be provided using clips.

Alternatively, the needle shield 25 may be formed out of thermoplastic elastomer (TPE) which is moulded on to the cap using an adhesive bond or glued thereto. Indeed, in some embodiments no tubular member 12a is provided and the needle shield is attached to the main body of the cap 12. The outer surface of the tubular member 12a is provided with a hook 12b or other suitable catch to which the distal end of an activation element 26 is attached.

The device 10 comprises a needle 17 which is held towards the proximal end of the needle 17 by a needle holder 18. The distal end of the needle is originally covered by the needle shield 25 which, in the embodiment shown in FIGS. 2-4, is inserted into the tubular member 12a of the cap 12 to form a frictional fit. As stated above, in alternative embodiments no tubular member 12a is provided. The needle holder 18 which holds the needle 17 is axially movable relative to the main body 11 and the cartridge 19. The needle holder has a generally cup-shaped portion 18a and a passage through which the needle 17 passes. The cup-shaped portion 18a is shaped to engage with the head 23 of the cartridge 19.

In some embodiments, the cup-shaped portion 18a of the needle holder 18 comprises a lip which serves to clip onto a head 23 of the medicament cartridge 19 to prevent detachment of the needle holder 18 from the cartridge 19 subsequent to attachment of the needle holder 18 to the cartridge 19. Alternatively, the needle holder 18 may be arranged to clip on to the cartridge holder 20.

The auto-injector device 10 comprises a cartridge 19 which is held in place by a cartridge holder 20. The cartridge holder 20 and cartridge 19 are connected and fixed relative to the main body 11 of the device 10. The cartridge 19 has a cartridge body 21 a neck 22 and a head 23. The head 23 is wider than the neck 22, thereby forming a flanged end. The neck 22 and head 23 contain a passage allowing medicament to pass therethrough as well as to receive the needle 17 once inserted. The head 23 is provided with a penetrable barrier such as a septum 24 to close off the passage and to seal the contents of the medicament cartridge 19. The cartridge body 21, neck 22 and head 23 may be generally cylindrical in shape. However, alternative shapes may be employed.

Figure 2B:
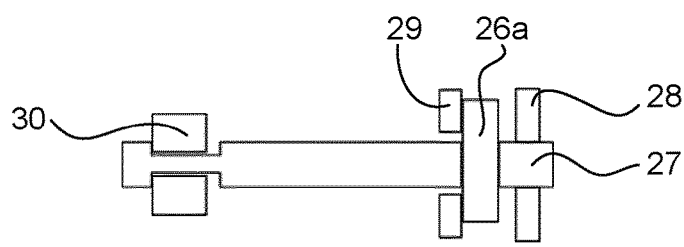
FIG. 2B is a schematic diagram of components of the device shown in FIG. 2A.
Figure 3:
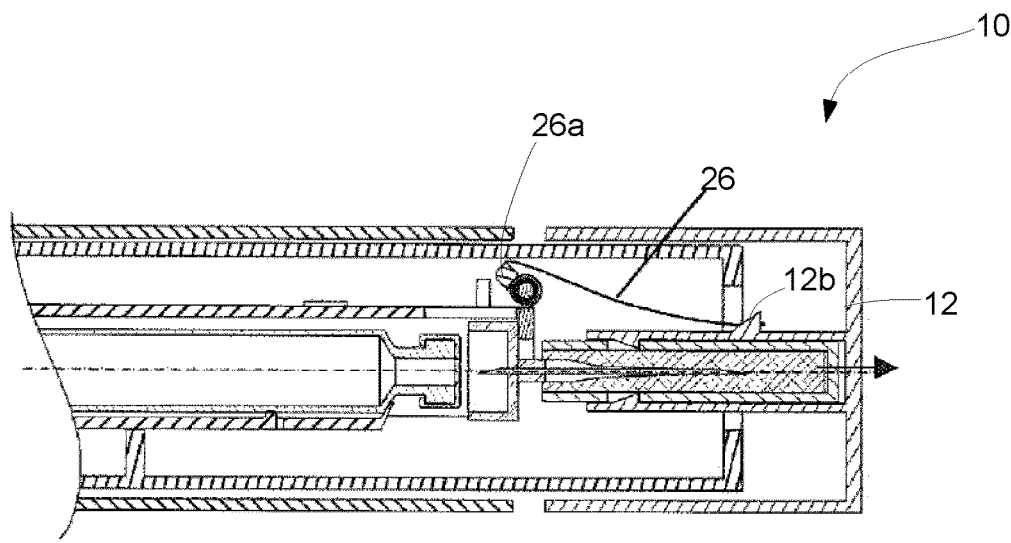
FIG. 3 is a side-on cross sectional schematic view of the distal end of the device shown in FIG. 2 during an early stage of cap removal.

Referring to FIGS. 2A and 2B, the cartridge holder 20 is provided with a constant force spring 27, a spring carrier 28 fixed to the needle holder 18 and a stopper 29 which is fixed with respect to the medicament cartridge. The constant force spring 27 may be a rolled ribbon of spring steel or other metal such that the spring is relaxed when it is fully roiled up. In alternative embodiments, the spring carrier 28 may form an integral part of the needle holder 18. The spring 27 is connected with the spring carrier 28 and pre-stressed by the activation element 26 having an activation element body 26a at a proximal end thereof which prevents the spring returning to its equilibrium position and the stopper 29 which holds the activation element body 26a in place. The proximal end of the spring 27 is fixed by a fixing element 30. The distal end of the activation element 26 is provided with a loop (not shown) which fits over the hook 12b located on the tubular member 12a. In alternative embodiments, the activation element 26 may be fixed to the main body of the cap 12.

FIG. 3 shows a cross section of the distal portion of the device 10 as the user pulls the cap 12 in an axial direction away from the main body 11 of the device 10. At the instant shown in FIG. 3, the user pulls on the cap 12 which thereby moves axially away from the main body 11 of the device 10. The hook 12b exerts a pulling force on the activation element 26. The activation element body 26a is displaced.

FIG. 4A shows a cross section of the distal portion of the device 10 as the spring 27 is released. At this instant, the activation element body 26a is decoupled from the spring 27. FIG. 4B shows schematically, the movement of the spring 27 and spring carrier 28. The coiled portion of the spring 27 winds onto the unwound portion causing the carrier 28 to move axially towards the medicament cartridge 19. The needle holder 18, which is fixed to carrier 28 and needle 17 also move axially towards the medicament cartridge 19. The proximal end of the needle 17 pierces the septum of the medicament cartridge 19.

The cup shaped part 18a of the needle holder 18 fits over the head 23 of the medicament cartridge 19 forming a frictional fit. In embodiments, having a lip around the inner edge of the cup shaped part 18a, the lip fits over the base of the head 23.

The cap 12 is thereby removed. The needle shield 25 is retained by the tubular member 12b of the cap 12. Once the cap has been removed, the distal end of the device 10 may be placed against the patient's injection site and the injection commenced.

FIG. 5 is a schematic diagram showing a device 50 according to an alternative embodiment. The device 50 comprises a cylindrical main body 51, a cap 52, a needle 53 held by an axially movable needle holder 54 and a medicament cartridge 55.

The main body 51 is generally cylindrical and has a collar 51a extending radially inwardly towards a neck 55a of the medicament cartridge 55. Alternatively, a medicament cartridge holder may be provided to hold the medicament cartridge 55 so that it is fixed with respect to the main body 51.

A pull spring 56 is attached, at one end thereof, to the collar 51a of the body 51 or medicament cartridge holder. At the other end, the pull spring 56 is attached to the needle holder 54. As shown in FIG. 5, the pull spring 56 is extended from its equilibrium length and is set under tension. During assembly of the device 50, the needle holder 54 is pulled away from the collar 51a or cartridge holder so that the pull-spring 56 is set under tension.

During assembly of the device, the connection of the pull-spring 56 on the cartridge holder and the connection of the pull-spring 56 on the needle holder 54 can be achieved by co-moulding, i.e. that the spring is directly inserted into the plastics moulding tool when moulding the parts. Alternatively, the pull spring 56 may be fixated using a clip or screwed in. In other embodiments, the spring can be attached with the help of hooks to the plastic parts. The pull-spring 56 may be manufactured from a metal (or other suitable material) that is strong enough to hold the needle holder 54 under tension during transit and storage of the device 50.

The cap 52 comprises a detent 57 such as an arm on the interior of the device cap 52 which holds the needle holder 54 in place so that the separation between the needle holder 54 and cartridge holder or collar 51a is maintained. The detent 57 acts as an activation element and prevents premature movement of the needle holder 54.

As shown in FIG. 6, as the user pulls the cap 52 from the main body 51 of the device, the detent 57 snaps over the needle holder 54. In some embodiments, the cap 52 may be squeezed towards the distal end thereof, causing the detent 57 to pivot outwards and disengage with the needle holder 54, as shown in FIG. 7. The pull-spring 56 is thereby released and shortens in length. In some embodiments, the detent 57 may be arranged so that it can only release the pull-spring once the cap 52 has been rotationally aligned with the needle holder 54. Due to the shortening of the pull-spring 57, the needle holder 54 is caused to move axially towards the cartridge holder or collar 51a. The needle 53 pierces the cartridge septum 55b with the proximal tip thereof. A fluid connection is thereby established between the medicament cartridge 55 and the needle 53.

The skilled person will recognise advantages provided by embodiments of the disclosure. For example, fewer user handling steps for the user compared with manual assembly of a needle to a device. The user steps of inserting the needle into the medicament cartridge and removing the cap are combined. This provides a reduced risk for needle stick injuries as the needle shield does not need to be detached separately.

Embodiments above are described with respect to auto-injectors. However, embodiments relating to other types of injectors, such as syringes, also fall within the scope of the disclosure.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15$^{th}$ edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten. An example of an oligonucleotide is, for example: mipomersen sodium (Kynamro®), a cholesterol-reducing antisense therapeutic for the treatment of familial hypercholesterolemia. Examples of DPP4 inhibitors are Vildagliptin, Sitagliptin, Denagliptin, Saxagliptin, Berberine. Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. A medicament delivery device, comprising:
   a main body arranged to receive a medicament cartridge sealed with a penetrable barrier;
   a needle holder directly coupled to and carrying a needle;
   a cap removably coupled to the needle holder; and
   a pre-stressed spring connected to the needle holder and to the main body,
   wherein when the pre-stressed spring is held in a pre-stressed state by an activation element, the activation element is directly coupled to the cap and to the main body or directly coupled to the cap and to the pre-stressed spring, prior to any movement of the cap in a distal direction away from the medicament delivery device, and
   wherein the activation element is arranged to release the pre-stressed spring from the pre-stressed state when the cap is pulled in the distal direction from the medicament delivery device, thereby decoupling the activation element from the main body if the activation element is directly coupled to the cap and to the main body in the pre-stressed state, or from the pre-stressed spring if the activation element is directly coupled to the cap and to the pre-stressed spring in the pre-stressed state, and causing the needle holder to move axially in a proximal direction.

2. The medicament delivery device of claim 1, wherein the needle holder comprises a cup-shaped part configured to form a frictional fit with the medicament cartridge.

3. The medicament delivery device of claim 2, wherein the cup-shaped part has a lip to grip the medicament cartridge or a cartridge holder.

4. The medicament delivery device of claim 1, further comprising a needle shield for shielding a distal end of the needle, wherein the needle shield is arranged to be fixed to the cap and removable from the needle.

5. The medicament delivery device of claim 1, wherein the main body comprises a cartridge holder for receiving the medicament cartridge.

6. The medicament delivery device of claim 5, wherein the pre-stressed spring is a constant force spring fixed, at a first end thereof, to the cartridge holder and fixed, at a second end thereof, to a spring carrier attached to the needle holder, and wherein the constant force spring is held in the pre-stressed state by a removable portion of the activation element.

7. The medicament delivery device of claim 5, wherein the pre-stressed spring is a pull spring attached, at a first end thereof, to the cartridge holder and attached, at a second end thereof, to the needle holder.

8. The medicament delivery device of claim 1, wherein the pre-stressed spring is a pull spring attached, at a first end thereof, to the main body and attached, at a second end thereof, to the needle holder.

9. The medicament delivery device of claim 8, wherein the activation element is a detent disposed on an interior region of the cap.

10. The medicament delivery device of claim 9, wherein the cap has pivotable side walls that are arranged to release the detent when the cap is squeezed.

11. The medicament delivery device of claim 9, wherein the detent is releasable after rotationally aligning the cap with the needle holder.

12. The medicament delivery device of claim 1, wherein the medicament delivery device contains the medicament cartridge and axial movement of the needle holder causes the needle to penetrate the penetrable barrier of the medicament cartridge.

13. The medicament delivery device of claim 12, wherein the medicament cartridge contains a medicament.

14. The medicament delivery device of claim 1, wherein the medicament delivery device is an auto-injector.

15. The medicament delivery device of claim 1, wherein the pre-stressed spring is directly connected to the needle holder and to the main body.

16. A method of operating a medicament injection device having a cap, the method comprising: holding a pre-stressed spring of the medicament injection device in a pre-stressed state with an activation element that is directly coupled to the cap and to the pre-stressed spring or directly coupled to the cap and to a main body of the medicament injection device prior to any pulling of the cap in a distal axial direction away from the medicament injection device; and after holding the pre-stressed spring in the pre-stressed state, pulling the cap in the distal axial direction to remove the cap from the medicament injection device to release the pre-stressed spring, thereby decoupling the activation element from the main body if the activation element is directly coupled to the cap and to the main body in the pre-stressed state, or from the pre-stressed spring if the activation element is directly coupled to the cap and to the pre-stressed spring in the pre-stressed state, and causing proximal movement of a needle holder directly coupled to and carrying a needle, to cause a proximal end of the needle to pierce a penetrable barrier of a medicament cartridge.

* * * * *